United States Patent
Torikoshi et al.

(10) Patent No.: US 7,957,910 B2
(45) Date of Patent: Jun. 7, 2011

(54) METHOD FOR PREDICTING EFFECTIVENESS OF CHEMOTHERAPY

(75) Inventors: Yasuhiro Torikoshi, Toyonaka (JP); Yuko Kawasaki, Kobe (JP); Satoshi Nakayama, Kobe (JP); Hideki Ishihara, Miki (JP); Tomoko Matsushima, Kobe (JP)

(73) Assignee: Sysmex Corporation, Hyogo (JP)

( * ) Notice: Subject to any disclaimer, the term of this patent is extended or adjusted under 35 U.S.C. 154(b) by 1288 days.

(21) Appl. No.: 11/330,137

(22) Filed: Jan. 12, 2006

(65) Prior Publication Data

US 2006/0173632 A1   Aug. 3, 2006

(30) Foreign Application Priority Data

Jan. 31, 2005  (JP) ................................. 2005-22593
May 31, 2005  (JP) ................................ 2005-158373

(51) Int. Cl.
   *G01N 33/48*  (2006.01)
   *C12Q 1/68*  (2006.01)
(52) U.S. Cl. ................................. 702/19; 435/6; 702/20
(58) Field of Classification Search ........................ None
   See application file for complete search history.

(56) References Cited

U.S. PATENT DOCUMENTS

| 6,521,407 B1 | 2/2003 | Warenius et al. |
| 2005/0131057 A1 | 6/2005 | Ueno et al. |

FOREIGN PATENT DOCUMENTS

| EP | 1 600 513 A1 | 11/2005 |
| GB | 2 334 578 A | 8/1999 |
| JP | 2003-199585 A | 7/2003 |
| JP | 2003-304884 A | 10/2003 |
| WO | WO 99/42834 A2 * | 8/1999 |

OTHER PUBLICATIONS

XP-002378582, Karen A. Rossi, et al, Understanding and Modulating Cyclind-Dependent Kinase Inhibitor Specicity: Molecular Modeling and Biochemical Evaluation of Pyrazolopyrimidinones as CDK2/Cylin A and CDK4/Cyclin D1 Inhibitors, Journal of Computer-Aided Molecular Design, 2005, 19, pp. 111-122.
XP-002979096, Jong Hun Kim, et al, Amplified CDK2 and CDC2 Activities in Primary Colorectal Carcinoma, Cancer, American Cancer Society, 1999, pp. 546-553.
XP-002114068, Seabra et al., Proceeding of the Annual Meeting of the American Association for Cancer Research, 1998, vol. 39, p. 442.

* cited by examiner

*Primary Examiner* — Shubo (Joe) Zhou
(74) *Attorney, Agent, or Firm* — Sughrue Mion, PLLC

(57) ABSTRACT

A method for predicting an effectiveness of chemotherapy is described. The method comprises a comparing step and a predicting step. The comparing step is a step of comparing a threshold value with a parameter of a cyclin dependent kinase (CDK) included in a sample containing a tumor cell obtained from a human patient. The predicting step is a step of predicting the effectiveness based on a comparison result of the comparing step. Above stated parameter is selected from the group consisting of an activity, an expression level, and a ratio of activity to expression level.

9 Claims, 3 Drawing Sheets

METHOD FOR PREDICTING EFFECTIVENESS OF CHEMOTHERAPY

TECHNICAL FIELD

The present invention relates to a method for predicting effectiveness of chemotherapy with high probability.

BACKGROUND ART

Chemotherapy is one of therapeutic methods for cancer. However, a specific anticancer agent may be effective for some patients but not for other patients.

Before chemotherapy, it is therefore preferable to know whether or not the anticancer agent is effective for an intended patient.

WO2004/076686 suggests that at least two kinds of proteins related to cell cycle are measured, and on the basis of measurement results, a drug tolerance test and prognosis are feasible.

SUMMARY

The present invention provides a method for predicting effectiveness of chemotherapy.

The scope of the present invention is defined solely by the appended claims, and is not affected to any degree by the statements within this summary.

A first aspect of the present invention relates to a method for predicting an effectiveness of chemotherapy using an anticancer agent, comprising:

a comparing step of comparing a threshold value with a parameter of a cyclin dependent kinase (CDK) included in a sample containing a tumor cell obtained from a human patient; and a predicting step of predicting the effectiveness based on a comparison result of said comparing step, wherein said parameter is selected from the group consisting of an activity, an expression level, and a ratio of activity to expression level.

A second aspect of the present invention relates to a method for predicting an effectiveness of chemotherapy using an anticancer agent, comprising:

a comparing step of comparing a threshold value with a parameter of a cyclin dependent kinase (CDK) included in a sample containing a tumor cell obtained from a human patient; and a predicting step of predicting that said chemotherapy to said human patient is effective based on a comparison result of said comparing step, wherein said parameter is selected from the group consisting of an activity, an expression level, and a ratio of activity to expression level.

A third aspect of the present invention relates to a method for predicting an effectiveness of chemosensitivity, comprising:

a comparing step of comparing a threshold value with a parameter of a cyclin dependent kinase (CDK) included in a sample containing a tumor cell obtained from a human patient; and a predicting step of predicting the chemosensitivity of said tumor cell based on a comparison result of said comparing step, wherein said parameter is selected from the group consisting of an activity, an expression level, and a ratio of activity to expression level.

DESCRIPTION OF THE PREFERRED EMBODIMENTS

Figure 1:
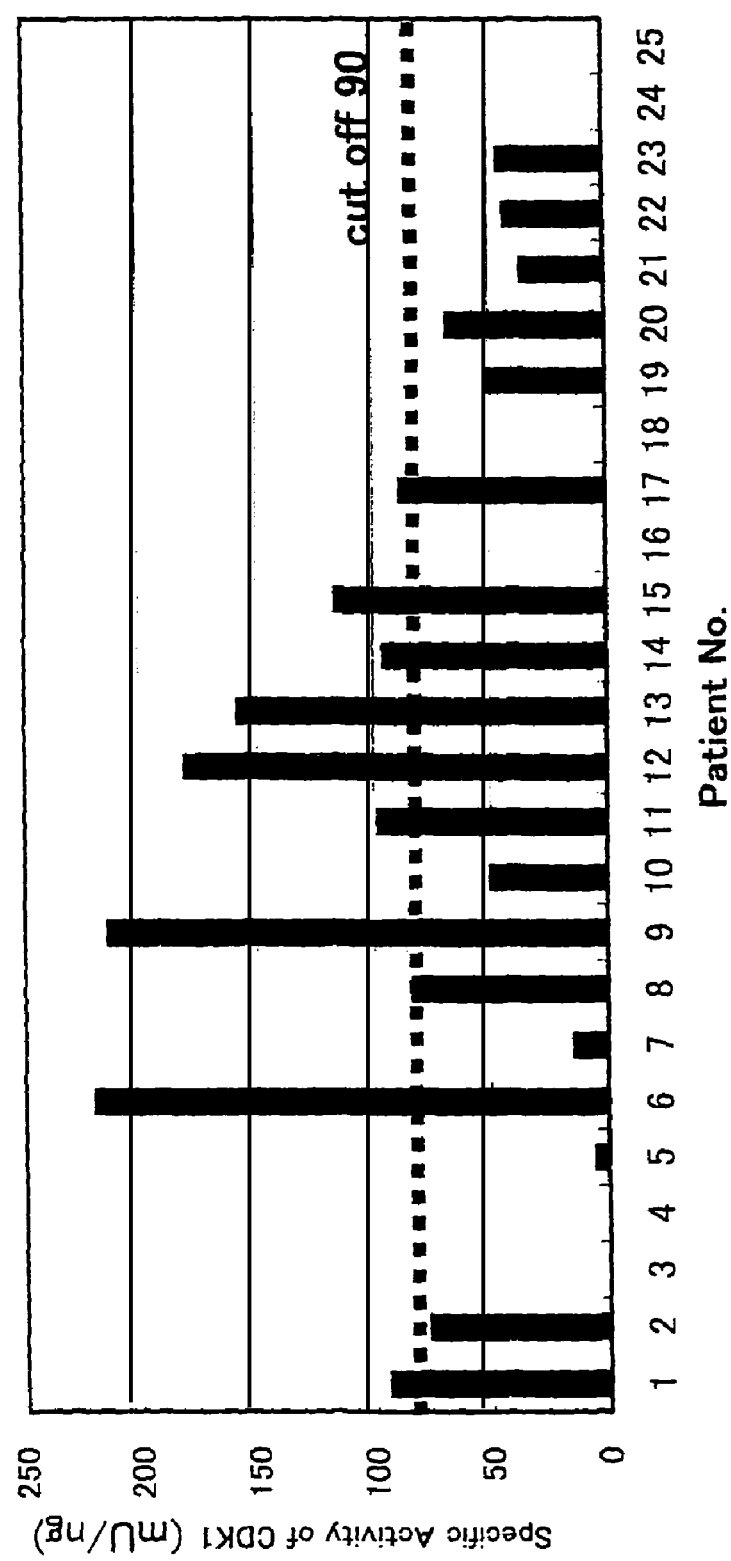
FIG. 1 is a graph showing the results of Experiment 1.

The method in this embodiment comprises a comparing step of comparing a specific parameter of a cyclin dependent kinase (CDK) of a tumor cell collected from a patient, with a threshold value corresponding to this parameter; and a predicting step of predicting the effectiveness of chemotherapy for the patient, on the basis of a comparison result of the comparing step.

According to this method, the sensitivity of a tumor cell collected from a patient to an anticancer agent can be determined, and the effectiveness of the anticancer agent for the patient can be predicted.

The "parameter" in this specification is selected from the group consisting of an activity, an expression level, and a ratio of activity to expression level.

The cyclin dependent kinase (CDK) used in the present invention may be one kind of CDK (method 1) or two or more kinds of CDKs (method 2).

When one kind of CDK is used, a parameter of CDK is compared with a threshold value corresponding to this parameter (comparing step). On the basis of this comparison result, the effectiveness of chemotherapy is predicted (predicting step).

When two or more kinds of CDKs are used, methods 2-1, 2-2 and 2-3 shown below can be used as the method 2 in this embodiment.

(Method 2-1)

A plurality of parameters of CDKs are compared respectively with threshold values corresponding to these parameters (comparing step). On the basis of a combination of the respective comparing results of CDKs, the effectiveness of chemotherapy for the patient is predicted (predicting step).

In the method 2-1, for example a first CDK parameter is compared with a threshold value corresponding to this parameter in the first comparing step, and a second CDK parameter is compared with a threshold value corresponding to this parameter in the second comparing step. Then, on the basis of the results of the first and second comparing steps, the effectiveness of chemotherapy for the patient is predicted.

(Method 2-2)

A first parameter of a first CDK is compared with a threshold value corresponding to this parameter (first comparing step). On the basis of a result of the first comparing step, the effectiveness of chemotherapy for the patient is predicted (first predicting step).

When effectiveness is not predicted in the first predicting step, a second parameter of a second CDK different from the first CDK is compared with a threshold value corresponding to this parameter (second predicting step). On the basis of a result of the second comparing step, the effectiveness of chemotherapy for the patient is predicted (second predicting step).

In the method 2-2, the parameter (first parameter) and the second parameter may be the same or different (for example, the expression level is used as the parameter of one CDK, and the activity is used as the parameter of the other CDK).

(Method 2-3)

A first parameter of a first CDK is compared with a threshold value corresponding to this parameter (first comparing step). On the basis of a result of the first comparing step, the effectiveness of chemotherapy for the patient is predicted (first predicting step).

When effectiveness is not predicted in the first predicting step, a second parameter of a second CDK is compared with a threshold value corresponding to this parameter (second comparing step). Further, a third parameter of a third CDK is compared with a threshold value corresponding to this parameter (third comparing step). On the basis of the results of the second and third comparing steps, the effectiveness of chemotherapy for the patient is predicted (second predicting step) A third method using a cyclin dependent kinase inhibitor (CDK inhibitor) may also be used. As the third method in this embodiment, methods 3-1 and 3-2 described below can be used.

(Method 3-1)

A parameter of CDK is compared with a threshold value corresponding to this parameter (first comparing step). Then, an expression level of CDK inhibitor is compared with a threshold value corresponding to this parameter (second comparing step). On the basis of a combination of the results of the first and second comparing steps, effectiveness is predicted (predicting step).

(Method 3-2)

A parameter of CDK is compared with a threshold value corresponding to this parameter (first comparing step). On the basis of a result of the first comparing step, effectiveness is predicted (first predicting step). When effectiveness is not determined in the first predicting step, an expression level of CDK inhibitor is compared with a threshold value corresponding to this parameter (second comparing step). On the basis of a result of the second comparing step, effectiveness is predicted (second predicting step).

The type of CDK is suitably selected depending on the type of cancer and the type of anticancer agent. The CDK is selected preferably from the group consisting of CDK1, CDK2, CDK4 and CDK6. The CDK inhibitor is a factor binding to a cyclin/CDK complex and inhibiting its activity. The CDK inhibitor is classified into INK4 family and CIP/KIP family. In the method in this embodiment, the CIP/KIP family is preferably used, and p21 is more preferably used.

In the method in this embodiment, the threshold value of CDK parameter or the threshold value of expression level of CDK inhibitor is preferably established in the following manner. Tumor cells are collected from a plurality of patients for whom the effectiveness of chemotherapy has been revealed. The parameter of CDK contained in the collected tumor cells is calculated. The above effectiveness is compared with the calculated value of the measured parameter to establish the threshold value.

When a malignant tumor is found in the living body, an operation for extirpation is conducted in some cases. "Chemotherapy" includes chemotherapy conducted before this operation (preoperative therapy) and chemotherapy after this operation (postoperative therapy). According to the method in this embodiment, the effectiveness of preoperative therapy and/or postoperative therapy can be predicted. When a primary lesion is shrunk or eliminated as a result of administration of an anticancer drug before the operation, preoperative therapy is effective. When recurrence is not recognized as a result of administration of an anticancer drug before the operation, postoperative therapy is effective.

The cells used in the method in this embodiment are tumor cells in tumor tissue extirpated from a patient. In the case of postoperative therapy, these cells can be obtained by an operation for extirpation. In the case of preoperative therapy, cells obtained by biopsy from a tumor tissue from a patient can be used.

A cyclin dependent kinase (CDK) is an enzyme to be activated by binding to cyclin. CDK functions in a specific period of cell cycle, depending on its type.

In this specification, the "cancer" includes adenocarcinoma, hematopoietic organ-derived cancer, sarcoma, etc. The type of cancer includes, for example, breast cancer, stomach cancer, colon cancer, esophagus cancer, prostate cancer, leukemia, osteosarcoma etc.

The "anticancer agent" in this specification refers to a chemical substance having an anticancer effect on the cancers mentioned above.

The "chemotherapy" in this specification is therapy for a malignant tumor in the living body by administering the anticancer agent into the living body.

Chemotherapy for breast cancer includes, for example, CMF therapy (therapy by administering a combination of 3 agents, those are, cyclophosphamide, methotrexate and fluorouracil), therapy using taxane-based anticancer agents such as docetaxel, paclitaxel etc., CE therapy (therapy by administering a combination of 2 agents, that is, cyclophosphamide and epirubicin), AC therapy (therapy by administering 2 agents, that is, doxorubicin and cyclophosphamide), CAF therapy (therapy by administering a combination of 3 agents, that is, fluorouracil, doxorubicin and cyclophosphamide), FEC therapy (therapy by administering a combination of 3 agents, that is, fluorouracil, epirubicin and cyclophosphamide), therapy by administering a combination of 2 agents, that is, trastuzumab and paclitaxel, and therapy using capecitabine.

Chemotherapy for stomach cancer includes, for example, FAM therapy (therapy by administering a combination of 3 agents, that is, fluorouracil, doxorubicin and mitomycin C), FAP therapy (therapy by administering a combination of 3 agents, that is, fluorouracil, doxorubicin and cisplatin), ECF therapy (therapy by administering a combination of 3 agents, that is, epirubicin, cisplatin and fluorouracil), therapy by administering a combination of 2 agents, that is, mitomycin C and tegafur, and therapy by administering a combination of 2 agents, that is, fluorouracil and carmustine.

Chemotherapy for colon cancer includes, for example, therapy by administering a combination of 2 agents, that is, fluorouracil and leucovorin and therapy by administering a combination of 2 agents, that is, mitomycin and fluorouracil.

Chemotherapy for ovary cancer includes, for example, TP therapy (therapy by administering a combination of 2 agents, that is, paclitaxel and cisplatin), TJ therapy (therapy by administering a combination of 2 agents, that is, paclitaxel and carboplatin), CP therapy (therapy by administering a combination of 2 agents, that is, cyclophosphamide and cisplatin), and CJ therapy (therapy by administering a combination of 2 agents, that is, cyclophosphamide and carboplatin).

The parameter of CDK is selected from the group consisting of an activity, an expression level, and a ratio of activity to expression level. The ratio of activity to expression level may be CDK specific activity (activity/expression level) or the reciprocal of CDK specific activity (expression level/activity).

Whether chemotherapy is effective or not can be determined by comparing the parameter with a specific threshold value. The type of CDK parameter can be suitably selected according to the type of anticancer agent and the type of cancer. The activity and expression level of CDK in a plurality of tumor cells against which the effectiveness of chemotherapy has been revealed are measured, and the parameter correlated most with the effectiveness is selected.

The method 2 in this embodiment is effective in increasing the probability of prediction. Even if the effectiveness of chemotherapy cannot be determined by the method 1, it is possible that chemotherapy is effective, and therefore the method 2 can be used to predict effectiveness.

The effectiveness of chemotherapy can be classified into a level in which morbidity is prevented from further deteriorating and a level in which a tumor is shrunk and morbidity is ameliorated. By the method in this embodiment, the effectiveness of chemotherapy can also be predicted.

As the factor of predicting therapeutic effectiveness in a CMF administration group, Her2 and p21 are reported. In a trial in the International Breast Cancer Study Group (IBCSG), it was revealed that administration of CMF is not effective for a patient with breast cancer expressing an excess of Her2. It is reported on p21 that rate of disease-free survival in a group of patients expressing p21 at high level is significantly lower than that in a group of patients expressing p21 at low level. However, both of Her2 and p21 are factors of predicting effectiveness in a group of patients for whom the effectiveness of CMF therapy is low, and there is no report on prediction of effectiveness in a group of patients for whom CMF therapy is therapeutically effective. On the other hand, the method in this embodiment can positively show effectiveness. Further, the case where effectiveness near to 100% can be expected can be shown by establishing the threshold value strictly.

The CDK activity is a value based on the amount of phosphoric acid introduced into a substrate by CDK contained in a sample. The CDK activity is a value (unit: U) calculated quantitatively from a measurement of a standard of a label (for example $^{32}P$, fluorescence) used in measurement of the amount of phosphoric acid. The method of measuring the CDK activity includes a method of measuring the activity by using a radioisotope and a method of measuring the activity by using adenosine 5'-O-(3-thiotriphosphate). According to the method of measuring the activity by using a radioisotope, a sample containing active CDK is prepared from a cell lysate of a specimen. Using $^{32}P$-labeled ATP ($\gamma$-[$^{32}P$]-ATP), $^{32}P$ is incorporated into a substrate protein by the action of CDK. The amount of the label in the labeled phosphorylated substrate is measured, and the CDK activity can be calculated on the basis of a calibration curve prepared using a standard.

According to the method of using adenosine 5'-O-(3-thiotriphosphate) (U.S. Publication No. 20020164673), a sample containing an objective active CDK is first prepared from a cell lysate of a specimen. Then, adenosine 5'-O-(3-thiotriphosphate) (ATP-$\gamma$S) is reacted with a substrate by the action of CDK, to introduce a monothiophosphoric acid group into a serine residue or a threonine residue of the substrate. A labeling fluorescence substance or a labeling enzyme is bound to a sulfur atom of the introduced monothiophosphoric acid group thereby labeling the substrate protein. The amount of the label (or the amount of fluorescence when a fluorescence label is used) of the labeled thiophosphorylated substrate is measured, and CDK activity can be calculated on the basis of a calibration curve prepared using a standard.

The objective CDK can be collected from a cell lysate. In this case, the CDK may be collected by using an anti-CDK antibody specific to the objective CDK. In the case of measurement of the activity of a specific cyclin dependent kinase (for example, cyclin A dependent kinase, cyclin B dependent kinase, cyclin E dependent kinase), the CDK may be collected by using an anti-cyclin antibody. In both the cases, CDKs besides the active CDK are collected. For example, a complex having the CDK inhibitor bound to a cyclin/CDK complex is also collected. When an anti-CDK antibody is used, the single CDK molecule, a complex of CDK and cyclin and/or CDK inhibitor, and a complex of CDK and another compound are collected. The activity is measured as unit (U) of the phosphorylated substrate under a condition where active and inactive CDKs and a wide variety of competitive reactions occur.

The cell lysate can be prepared by adding a buffer to a biological sample containing tumor cells, then homogenizing the cells and releasing substances present in the cell membrane or in the nuclear membrane into the buffer. A surfactant, a protease inhibitor etc. may be added if necessary to the buffer.

The expression level of CDK is the amount of objective CDK measured in the cell lysate, and can be measured in a conventionally known method of measuring the mass of the objective protein in a protein mixture. For example, the ELISA method, Western blotting method etc. can be used. The objective protein (CDK) may be captured by using a specific antibody. For example, an anti-CDK1 antibody can be used to capture every CDK1 (including the single CDK molecule, a complex of CDK and cyclin and/or CDK inhibitor, and a complex of CDK and another compound).

The ratio of CDK activity/CDK expression level (CDK specific activity) or CDK expression level/CDK activity corresponds to the ratio of the active CDK in all CDKs present in a cell. Particularly, a cell lysate prepared from a sample obtained by biopsy is easily influenced by the amount of non-cellular tissues (for example extracellular stroma) contained in actually collected tissues. Accordingly, the CDK activity/expression level ratio can be used to eliminate inevitable influence at the time of preparation of a measurement sample.

The expression level of CDK inhibitor is the amount of the objective CDK inhibitor measured in a cell lysate, and can be measured in a known method. For example, the ELISA method, Western blotting method etc. may be used.

EXPERIMENTS (1) Measurement of CDK Activity

A mixture of a buffer and a sample (cell lysate) prepared from tissues containing tumor cells was introduced into a 1.5-ml Eppendorf tube. The sample was introduced such that the total protein mass became 100 μg in 500 μl of the mixture.

2 μg CDK-specific antibody (polyclonal anti-CDK1 antibody or polyclonal anti-CDK2 antibody: Santa Cruz Biotechnology, Inc.) and 20 μl protein A-coated Sepharose beads (Bio-Rad Laboratories, Inc.) were added to the above mixture and reacted at 4° C. for 1 hour. Thereafter, the beads were washed 3 times with a washing buffer (0.1% Nonidet P-40 (NP-40), 50 mM Tris-HCl, pH 7.0). The Sepharose beads were suspended in 15 μl kinase buffer to give a sample containing the beads to which the objective CDK had been bound.

A substrate solution (containing 10 μg histone H1 (Upstate Biotechnology, Inc.) as a substrate of CDK, 5 mM adenosine 5'-O-(8-thio-3-phosphoric acid) (ATP-$\gamma$S, manufactured by Sigma) and a buffer (20 mM Tris-HCl (pH 7.4), 0.1% Triton X-100)) was prepared. This substrate solution was added to the above sample to give 50 μl mixture, and this mixture was then incubated at 37° C. for 10 minutes under shaking. Serine residues or threonine residues of the substrate were phosphorylated by the action of active CDK to give a monothiophosphorylated substrate.

After the enzyme reaction, the mixture was centrifuged at 2000 rpm for 20 seconds to precipitate the beads, and 18 μl supernatant containing the monothiophosphorylated substrate was collected. 15 μl labeling buffer (containing 150 mM Tris-HCl (pH 9.2), and 5 mM EDTA) was added to the supernatant and incubated for 90 minutes in 10 mM iodoacetyl biotin solution (100 mM Tris-HCl (pH 7.5), 1 mM EDTA) in a dark place at room temperature, whereby sulfur in the thiophosphoric acid of the monothiophosphorylated substrate was labeled with biotin. The reaction of iodoacetyl biotin with thiophosphoric acid was terminated by adding 6-mercaptoethanol.

0.4 μg of the biotin-labeled thiophosphorylated substrate was added onto a PVDF membrane by a slot blotter and suctioned at negative pressure from the bottom of the membrane. The resulting membrane was blocked with 1% bovine serum albumin (BSA) for 30 minutes and reacted with avidin-FITC (manufactured by Vector) at 37° C. for 1 hour. Thereafter, the membrane was washed for 10 minutes 3 times with 50 mM TBS (containing 25 mM Tris-HCl (pH 7.4), and 150 mM NaCl). After washing, the membrane was analyzed by a fluorescence image analyzer (manufactured by Bio-Rad Laboratories, Inc.). The activity was calculated based on a calibration curve.

The calibration curve was prepared in the following manner. A protein (biotin-labeled immunoglobulin) of known amount was adsorbed onto a PVDF membrane. The protein was labeled with FITC by the same manner as described above, and the fluorescent intensity was measured with a fluorescence image analyzer (manufactured by Bio-Rad Laboratories, Inc.). One U of CDK activity measured refers to a value showing equivalent fluorescent intensity to the amount of fluorescence where the protein is 1 ng.

(2) Measurement of CDK Expression Level

50 μl cell lysate prepared from tissues containing tumor cells was injected into each well (2×2×3 mm, acceptable amount 100 μl) of a slot blotter in which a PVDF membrane (Millipore Corporation) initialized by dipping in TBS (containing 25 mM Tris-HCl (pH 7.4), and 150 mM NaCl) had been set. Each well contained a total of 5 to 15 μg protein.

After the cell lysate was injected, the protein in the sample was adsorbed onto the membrane under suction at a negative pressure of about 150 mmHg for about 50 seconds from the backside of the membrane.

A solution of a primary antibody (rabbit anti-CDK1 antibody, rabbit anti-CDK2 antibody or rabbit anti-CDK4 antibody) was injected into each well and left at room temperature for about 30 minutes. The backside of the membrane was suctioned at a negative pressure of 500 mmHg for about 50 seconds. Thereafter, the membrane was washed with TBS (containing 25 mM Tris-HCl (pH 7.4), and 150 mM NaCl).

Then, a solution of a secondary antibody (biotinated anti-rabbit antibody) was injected into each well and left at room temperature for about 30 minutes. The secondary antibody solution was suctioned at a negative pressure of 500 mmHg for about 50 seconds from the backside of the membrane. Thereafter, the membrane was washed with TBS (containing 25 mM Tris-HCl (pH 7.4), and 150 mM NaCl).

40 μl FITC-labeled streptavidin reagent was injected into each well and left for about 30 minutes at room temperature, whereby the secondary antibody was labeled with FITC. This reagent was suctioned at a negative pressure of 500 mmHg for about 50 seconds from the backside of the membrane. Thereafter, the membrane was washed with TBS (containing 25 mM Tris-HCl (pH 7.4), and 150 mM NaCl).

The PVDF membrane was removed from the plate, then washed with distilled water and dipped in 20% methanol for 5 minutes. Then, the membrane was dried for about 15 minutes at room temperature, and then the fluorescent intensity of the protein adsorbed onto the membrane was measured by an image analyzer (Bio-Rad Laboratories, Inc.). On the basis of a measurement result and a previously prepared calibration curve, FITC-labeled protein (CDK1, CDK2 or CDK4) was calculated (in terms of the weight (ng) of the standard protein corresponding to the number of CDKs).

The calibration curve was prepared in the following manner. A pure recombinant CDK protein was dissolved at 5 levels of concentration in TBS (containing 0.005% NP-40 and 50 μg/ml BSA). This solution was adsorbed onto a membrane by injecting 50 μl of the solution into each well treated in the same manner as described above. The membrane was labeled with FITC in the same manner as described above, and the fluorescent intensity of the membrane was measured. On the basis of the fluorescent intensity, a calibration curve was prepared.

(3) Calculation of CDK Specific Activity

From the values of CDK activity and CDK expression level measured above, CDK specific activity (mU/ng) was calculated according to the following formula:

CDK specific activity=CDK activity/CDK expression level (4) Expression Level of p21

CALBIOCHEM p21 WAF1 ELISA kit (EMD Bioscience, Inc.) was used in quantification.

WAF1 standard (20 unit/ml lyophilized WAF1) was diluted serially with a cell lysate as a sample to give waf1 sample solutions (mixtures of the WAF1 standard and the sample). In each sample solution, the cell lysate had been diluted 4-fold or more.

100 μl of the above WAF1 sample solution or WAF1 standard was added to each well of a 96-well plastic well on which a rabbit polyclonal antibody (primary antibody) specific to WAF1 had been immobilized. The plate was sealed and incubated at room temperature for 2 hours, whereby the sample solution or standard was reacted with the primary antibody.

Each well was washed 3 times with a washing buffer (prepared by adding 25 ml of 20-fold conc. buffer to 475 ml deionized water), and then 100 μl detection antibody (biotinated anti-WAF1 monoclonal antibody) was added to each well. This plate was sealed and incubated at room temperature for 1 hour.

Each well was washed 3 times with the washing buffer. Thereafter, 100 μl dilution of peroxidase-bound streptavidin was added to each well and stirred gently. The plate was sealed and incubated at room temperature for 30 minutes. The unreacted peroxidase-bound streptavidin was removed.

After each well was washed 3 times with the washing buffer, 100 μl substrate solution (coloring substrate) was added to each well and reacted at room temperature for 30 minutes at room temperature in a dark place. After 30 minutes, the reaction was terminated by adding 100 μl termination solution (2.5 N sulfuric acid) to each well. The absorbance of each well was measured at 450/540 nm with a plate reader.

From a calibration curve prepared using the WAF1 standard, the concentration of p21 WAF1 in the WAF1 sample solution was calculated.

Experiment 1

Prediction of the Effectiveness of Chemotherapy Based on the Specific Activity of CDK1

(1) Preparation of Tumor Cells and a Sample (Cell Lysate)

As the tumor cells used in measurement, tumor cells extirpated from 25 patients with breast cancer (Patient Nos. 1 to 25) were used. These had been stored for 5 to 6 years. Before an operation for extirpation, chemotherapy had not been conducted.

After the operation for extirpation, these 25 patients received therapy by administration of CMF, and thereafter, Patient Nos. 1 to 16 did not indicate recurrence, while Patient Nos. 17 to 25 indicated recurrence, as shown in Table 1.

TABLE 1

| Patient No. | LN | T | HG | Stage | Recurrence | Site of recurrence |
|---|---|---|---|---|---|---|
| 1 | a | b | 2 | IIA | 0 | |
| 2 | a | b | 3 | IIA | 0 | |
| 3 | a | b | 3 | IIA | 0 | |
| 4 | a | b | No. Info. | IIA | 0 | |
| 5 | a | b | No. Info. | IIA | 0 | |
| 6 | b | a | 2 | IIA | 0 | |
| 7 | b | a | 3 | IIA | 0 | |
| 8 | b | b | 1 | IIB | 0 | |
| 9 | b | b | 3 | IIB | 0 | |
| 10 | b | b | No. Info. | IIB | 0 | |
| 11 | b | b | No. Info. | IIB | 0 | |
| 12 | b | b | No. Info. | IIB | 0 | |
| 13 | b | b | No. Info. | IIB | 0 | |
| 14 | c | b | 2 | IIB | 0 | |
| 15 | c | b | 2 | IIB | 0 | |
| 16 | c | b | 3 | IIB | 0 | |
| 17 | a | a | 1 | I | 1 | Lung |
| 18 | a | b | 2 | IIA | 1 | Lung |
| 19 | a | b | 3 | IIA | 1 | Lung |
| 20 | b | b | 1 | IIB | 1 | Bone |
| 21 | b | b | 2 | IIB | 1 | Cervical lymph node |
| 22 | b | b | 3 | IIB | 1 | Bone, Lung, Brain |
| 23 | c | a | 2 | >IIIA | 1 | Supra-clavicular lymph node |
| 24 | c | b | 2 | >IIIA | 1 | Bone |
| 25 | c | b | 3 | >IIIA | 1 | Bone |

In the table, "LN" shows the presence or absence of lymph node metastasis. In the item "LN", "a" shows that the metastasis of tumor cells to lymph nodes was not recognized. "b" shows that tumor cells metastasized to one to three lymph nodes. "c" shows that tumor cells metastasized to four or more lymph nodes.

In the table, "T" shows the size of tumor mass. In the item "T", "a" shows that the tumor diameter is less than 2 cm. "b" shows that the tumor diameter is 2 cm to less than 5 cm. "c" shows that the tumor diameter is 5 cm or more.

In the table, "HG" shows cancer histological grade. In the item "HG", "1" shows low grade. "2" shows that the grade of a typism is moderate. "3" shows that the grade of a typism is high.

In the table, "Stage" shows the TNM classification of breast cancer. In the item "Stage", "I" indicates Stage I (LN=a and T=a) in the TNM classification. "IIA" indicates Stage IIA (LN=a and T=b, or LN=b and T=a) in the TNM classification. "IIB" indicates Stage IIB (LN=b and T=b) in the TNM classification. ">IIIA" indicates Stage IIIA, Stage IIIB or Stage IV in the TNM classification.

In the table, the item "Recurrence" shows that recurrence occurred or did not occur after CMF therapy conducted after the operation for extirpation of breast cancer. In the item "Recurrence", "0" shows that recurrence did not occur. "1" shows that recurrence occurred.

In the table, the item "Site of recurrence" shows a site where recurrence occurred after the operation for extirpation of breast cancer.

In the table, "No. Info" shows that no information was obtained.

Tumor cells from each of Patient Nos. 1 to 25 were added to a lysis buffer (containing 0.1 w/v % Nonidet P-40 (NP-40) (manufactured by Calbiochem), 50 mM Tris-HCl (pH 7.4), 5 mM EDTA, 50 mM sodium fluoride, 1 mM sodium orthovanadate and 100 μl/ml protease inhibitor cocktail (Sigma)). The breast tumor cells were homogenized in this buffer with an electric homogenizer.

The resulting homogenate was centrifuged at 15000 rpm for 5 minutes at 4° C. to collect a supernatant (cell lysate).

(2) Correlation of CDK1 Specific Activity with Postoperative Recurrence

According to the measurement method described above, the cell lysate prepared in (1) above was measured for CDK1 activity and CDK1 expression level, to determine specific activity.

The CDK1 specific activity of each sample is shown in FIG. 1. When 90 was set as threshold value, CMF therapy was determined to be effective in 8 patients (Nos. 1, 6, 9, 11 to 15) showing a specific activity of 90 or more. From Table 1, recurrence was not confirmed in these 8 patients.

From the foregoing, it was revealed that by measuring the specific activity of CDK1 and comparing it with a predetermined threshold value, tumor cells in the above 8 patients (Nos. 1, 6, 9, 11 to 15) can be known to be chemosensitive to CMF, and CMF therapy for these patients can be predicted to be effective.

Experiment 2

Figure 2:
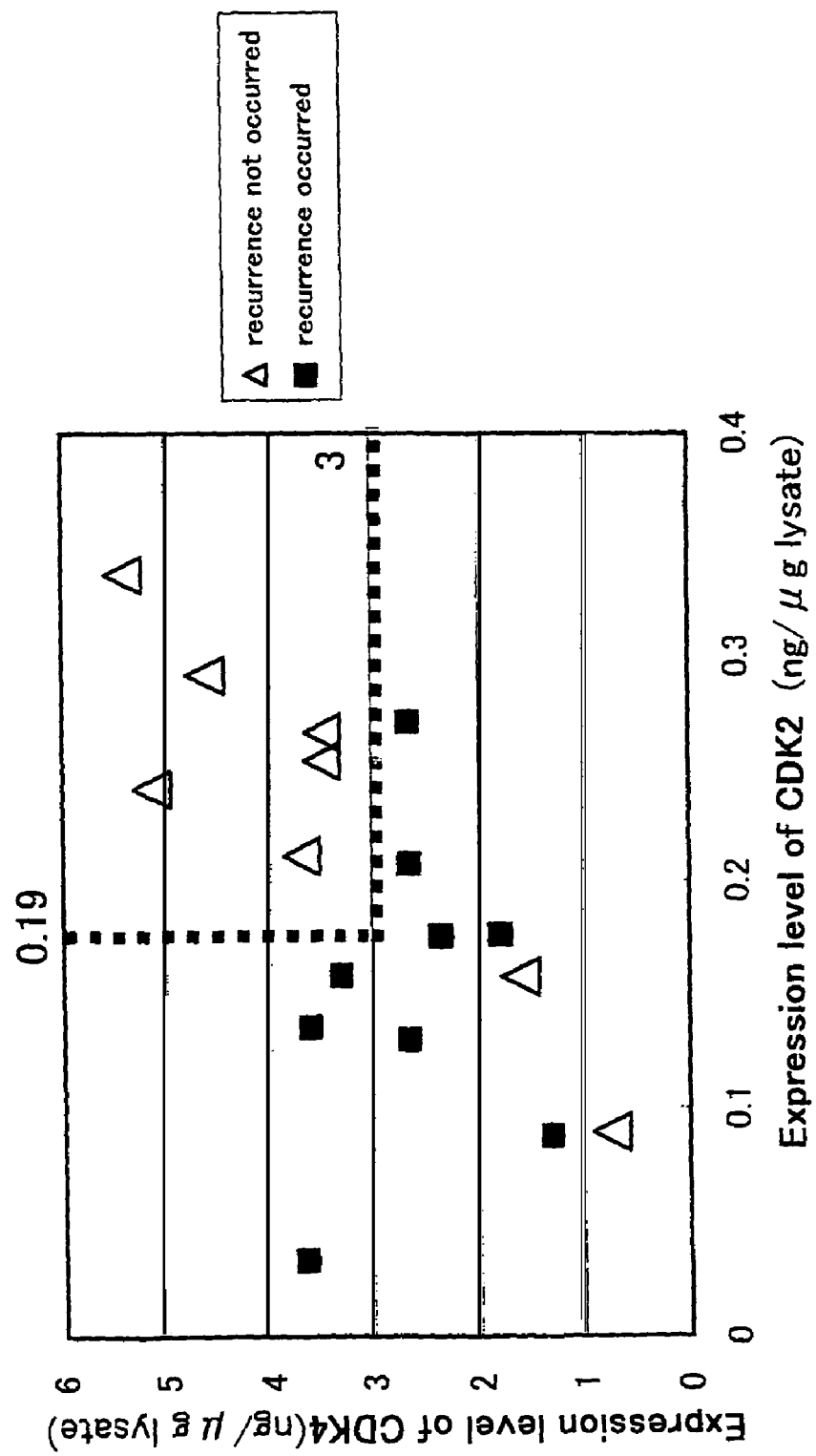
FIG. 2 is a graph showing the results of Experiment 2.

Prediction, Based on CDK2 and CDK4 Expression Levels, of the Effectiveness of Chemotherapy Tumor cells in the patients (Patient Nos. 2 to 5, 7, 8, 10, 16 to 25) showing a specific activity of less than 90 in Experiment 1 were used to measure the expression levels of CDK2 and CDK4 (ng/μg lysate) The results are shown in FIG. 2.

The threshold value of CDK2 was established to be 0.19, and the threshold value of CDK4 was established to be 3. When the expression level of CDK2 was the threshold value or more and simultaneously the expression level of CDK4 was the threshold value or more, CMF therapy was predicted to be effective. When the expression level of CDK2 was less than the threshold value or the expression level of CDK4 was less than the threshold value, the effectiveness of CMF therapy was predicted to be low.

From FIG. 2 and Table 1, it was confirmed that when the expression level of CDK2 is the threshold value or more and simultaneously the expression level of CDK4 is the threshold value or more, CMF therapy except for 2 cases is effective without recurrence after CMF therapy. When the expression level of CDK2 was less than the threshold value or the expression level of CDK4 was less than the threshold value, recurrence occurred after CMF therapy except for 2 cases, and the effectiveness of CMF therapy was confirmed to be low. From the foregoing, it was revealed that even if no effectiveness can be determined by prediction based on the specific activity of CDK1, the effectiveness of chemotherapy can be determined with high probability by prediction based on the expression levels of CDK2 and CDK4.

Experiment 3

Prediction, Based on CDK2 and p21, of the Effectiveness of Chemotherapy (1) Preparation of Cell Lysates Five kinds of human-derived breast cancer cultured cells (cells A to E) were transplanted subcutaneously into the back of mice, and the mice were maintained for 21 to 28 days to graft the breast tumor cells thereon. 50 mice (Nos. 1 to 50 (Table 2)) on which the breast tumor cells had been grafted were thus created. From the back of each of these mice, a 2.5 mm×2.5 mm tissue section (about 50 mg) was cut off, and a lysis buffer (containing 0.1 w/v % Nonidet P-40 (NP-40) (manufactured by Calbiochem), 50 mM Tris-HCl (pH 7.4), 5 mM EDTA, 50 mM sodium fluoride, 1 mM sodium orthovanadate and 100 µl/ml protease cocktail (Sigma)) was added to this tissue section. The tissue section in the lysis buffer was homogenized with an electric homogenizer.

The resulting homogenate was centrifuged at 15000 rpm for 5 minutes at 4° C. to collect a supernatant (cell lysate).

(2) Measurement and Judgment of CDK2 Specific Activity

According to the method of measuring the activity of CDK and the method of measuring the expression level of CDK as described above, the activity of CDK2 and the expression level of CDK2 in the cell lysate prepared in (1) above were measured to determine the specific activity of CDK2.

(3) Measurement of p21 Expression Level

According to the method of measuring the expression level of p21 as described above, the expression level of p21 in the cell lysate prepared in (1) above was measured.

(4) Effect of Chemotherapy on Mice Nos. 1 to 50

20 mg/kg (mouse weight)/day of paclitaxel was administered once a day into each of mice Nos. 1 to 50 for 5 day. The tumor size from the initiation of administration to day 11 was measured. Depending on change in tumor size, mice Nos. 1 to 50 were classified into types I, II and III. Type I mouse is a mouse confirmed to highly sensitive to the anticancer agent. By administering paclitaxel into this type of mouse, the tumor almost disappeared. Type II mouse is a mouse whose sensitivity to the anticancer agent was confirmed to be moderate. By administering paclitaxel into this type of mouse, the increase in tumor size is suppressed. Type III mouse is a mouse confirmed to be poor in sensitivity to the anticancer agent. Even if paclitaxel is administered into this type of mouse, the tumor size continues increasing. Type of each mouse is indicated in Table 2, item "result of (4)."

(5) Prediction of the Effectiveness of Chemotherapy

The cutoff value of the specific activity of CDK2 was established to be 400, and whether each mouse was "High" (400 or more) or "Low" (less than 400) was determined. The cutoff value of the expression level of p21 was established to be 8, and whether each mouse was "High" (8 or more) or "Low" (less than 8) was determined.

Figure 3:
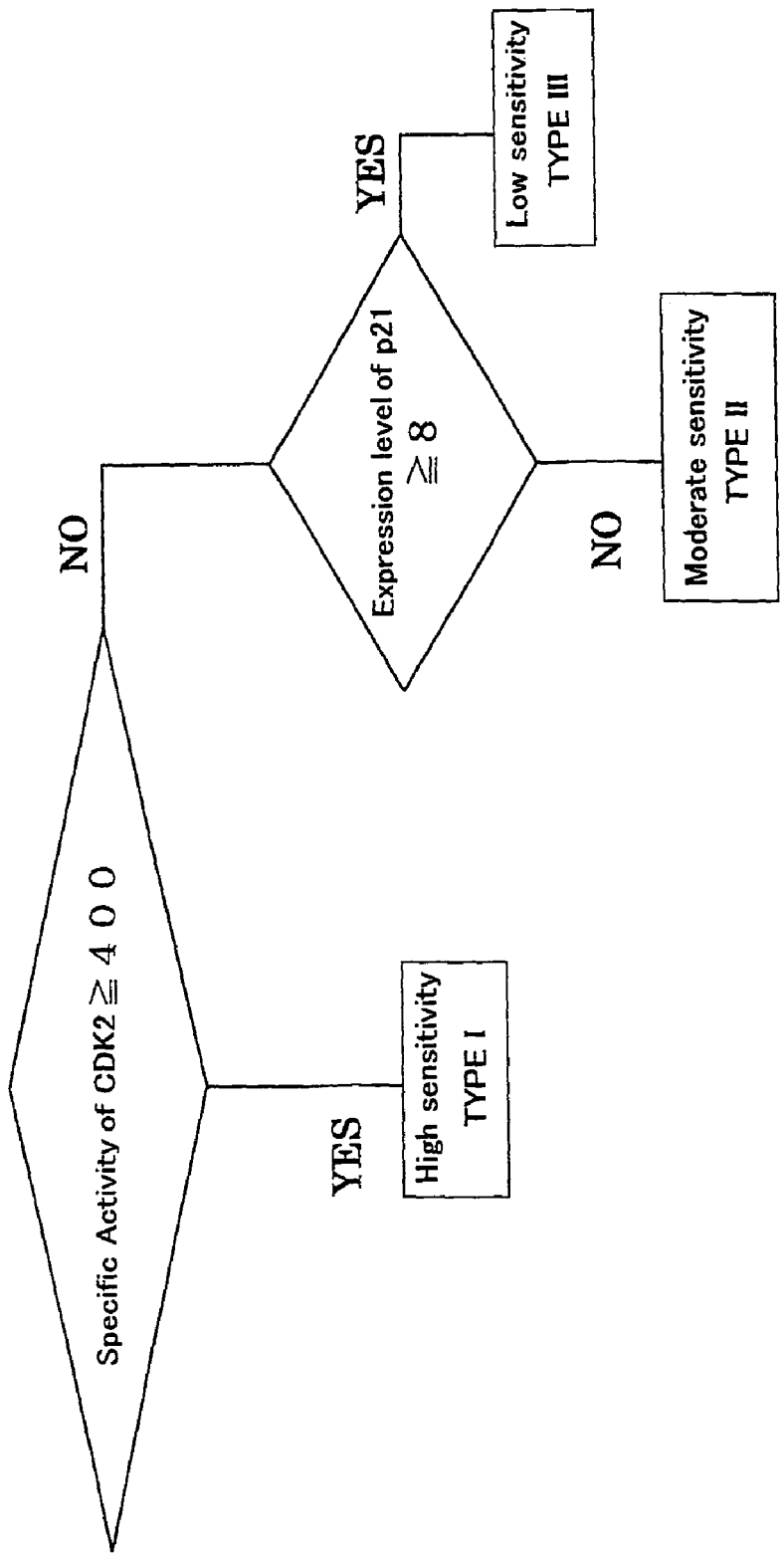
FIG. 3 is a flowchart used in Experiment 3.

According to the flowchart shown in FIG. 3, it was determined whether each mouse is type I (with high sensitivity to the drug), type II (with moderate sensitivity to the drug) or type III (with low sensitivity to the drug), on the basis of the specific activity of CDK2 and the expression level of p21. The respective measurements and judgment results are shown in Table 2, item "prediction by (5)."

The threshold value was established such that the percentage of correct answers from parameter measurements in the 50 mice became highest in relationship with the effectiveness of chemotherapy.

TABLE 2

| mouse No. | Cell | result of (4) | cdk2 specific activity | threshold 400 | p21 | threshold 8 | prediction by (5) | right or wrong |
|---|---|---|---|---|---|---|---|---|
| 1 | A | Type I | 1239.0 | High | 0.71" | Low" | Type I | right |
| 2 | A | Type I | 1172.9 | High | 1.01 | Low | Type I | right |
| 3 | A | Type I | 1221.4 | High | 1.21 | Low | Type I | right |
| 4 | A | Type I | 1426.8 | High | 1.15 | Low | Type I | right |
| 5 | B | Type II | 99.2 | Low | 6.82 | Low | Type II | right |
| 6 | B | Type II | 127.1 | Low | 4.48 | Low | Type II | right |
| 7 | B | Type II | 182.2 | Low | 5.92 | Low | Type II | right |
| 8 | B | Type II | 150.8 | Low | 9.43 | High | Type III | wrong |
| 9 | B | Type II | 190.5 | Low | 5.82 | Low | Type II | right |
| 10 | B | Type II | 106.7 | Low | 7.19 | Low | Type II | right |
| 11 | B | Type II | 111.9 | Low | 3.66 | Low | Type II | right |
| 12 | B | Type II | 156.8 | Low | 3.20 | Low | Type II | right |
| 13 | B | Type II | 228.0 | Low | 5.21 | Low | Type II | right |
| 14 | B | Type II | 120.3 | Low | 3.24 | Low | Type II | right |
| 15 | B | Type II | 15.5 | Low | 6.79 | Low | Type II | right |
| 16 | B | Type II | 113.1 | Low | 7.61 | Low | Type II | right |
| 17 | B | Type II | 79.0 | Low | 5.39 | Low | Type II | right |
| 18 | B | Type II | 99.4 | Low | 0.00 | Low | Type II | right |
| 19 | C | Type II | 140.3 | Low | 7.97 | Low | Type II | right |
| 20 | C | Type II | 137.9 | Low | 4.93 | Low | Type II | right |
| 21 | C | Type II | 148.2 | Low | 5.16 | Low | Type II | right |
| 22 | C | Type II | 162.0 | Low | 5.46 | Low | Type II | right |
| 23 | C | Type II | 240.7 | Low | 1.85 | Low | Type II | right |
| 24 | C | Type II | 204.7 | Low | 1.59 | Low | Type II | right |
| 25 | C | Type II | 129.6 | Low | 1.09 | Low | Type II | right |
| 26 | C | Type II | 169.9 | Low | 1.14 | Low | Type II | right |
| 27 | C | Type II | 127.6 | Low | 1.14 | Low | Type II | right |
| 28 | C | Type II | 98.8 | Low | 1.13 | Low | Type II | right |
| 29 | C | Type II | 57.0 | Low | 0.77 | Low | Type II | right |
| 30 | C | Type II | 80.7 | Low | 1.49 | Low | Type II | right |
| 31 | C | Type II | 177.2 | Low | 1.34 | Low | Type II | right |
| 32 | C | Type II | 134.3 | Low | 0.00 | Low | Type II | right |
| 33 | C | Type II | 89.8 | Low | 1.71 | Low | Type II | right |

TABLE 2-continued

| mouse No. | Cell | result of (4) | cdk2 specific activity | | p21 | | prediction by (5) | right or wrong |
|---|---|---|---|---|---|---|---|---|
| | | | | threshold 400 | | threshold 8 | | |
| 34 | C | Type II | 96.3 | Low | 0.53 | Low | Type II | right |
| 35 | C | Type II | 212.6 | Low | 0.82 | Low | Type II | right |
| 36 | C | Type II | 195.7 | Low | 1.18 | Low | Type II | right |
| 37 | D | Type III | 137.0 | Low | 2.69 | Low | Type II | wrong |
| 38 | D | Type III | 15.8 | Low | 4.85 | Low | Type II | wrong |
| 39 | D | Type III | 112.4 | Low | 8.61 | High | Type III | right |
| 40 | D | Type III | 2.9 | Low | 8.50 | High | Type III | right |
| 41 | D | Type III | 182.2 | Low | 5.58 | Low | Type II | wrong |
| 42 | D | Type III | 25.4 | Low | 0.71 | Low | Type II | wrong |
| 43 | E | Type III | 80.7 | Low | 29.20 | High | Type III | right |
| 44 | E | Type III | 73.2 | Low | 25.93 | High | Type III | right |
| 45 | E | Type III | 97.9 | Low | 21.10 | High | Type III | right |
| 46 | E | Type III | 63.0 | Low | 17.47 | High | Type III | right |
| 47 | E | Type III | 69.0 | Low | 3.52 | Low | Type II | wrong |
| 48 | E | Type III | 59.3 | Low | 5.22 | Low | Type II | wrong |
| 49 | E | Type III | 0.0 | Low | 14.95 | High | Type III | right |
| 50 | E | Type III | 47.2 | Low | 9.65 | High | Type III | right |

When the prediction result of effectiveness by using CDK2 and CDK inhibitor in (5) (referred to as prediction by (5) in Table 2) and the result of actual administration of the anticancer agent in (4) (referred to as result of (4) in Table 2) are identical with each other, "right" is given while these results are different from each other, "wrong" is given in Table 2.

As shown in Table 2, the comparison of the specific activity of CDK2 with the threshold value (=400) revealed that the mice showing a specific activity higher than the threshold value were classified into type I, and the mice showing a specific activity lower than the threshold value were classified into type II or III. Accordingly, the effectiveness of chemotherapy could be predicted with 100% probability by comparing the specific activity of CDK2 with the threshold value.

The comparison of the expression level of p21 with the threshold value (=8) revealed that the mice showing an expression level lower than the threshold value, except for mouse No. 8 (which was classified into type III), were classified into type I or II. The mice showing an expression level higher than the threshold value, except for mice Nos. 37, 38, 41, 42, 47 and 48, were classified into type III. Accordingly, the disappearance or shrinkage of the tumor by chemotherapy could be predicted with high probability by comparing the expression level of p21 with the threshold value.

The result of prediction of the effectiveness of chemotherapy according to the flowchart in FIG. 3 was consistent, with high probability, with the result of actual chemotherapy by (4). That is, as shown in Table 2, 7 of 50 cases were wrong (percentage of correct answers: 86%), and particularly in types I and II, for which chemotherapy was determined to be effective, only 1 of 36 cases was wrong where the percentage of correct answers was 97%.

As described above, the effectiveness of chemotherapy could be predicted with high probability by using two factors, that is, CDK2 and the CDK inhibitor, and comparing them with their threshold values.

What is claimed is:

1. A method for predicting an effectiveness of chemotherapy using an anticancer agent, comprising steps of:
   measuring an activity of a cyclin dependent kinase 1 (CDK1) and an expression level of the CDK1, an expression level of a CDK2 and an expression level of a CDK4 included in a sample containing a tumor cell obtained from a human patient by a measuring device;
   calculating a specific activity representing a ratio of the measured CDK1 activity and CDK1 expression level by calculator;
   comparing a threshold value with the calculated CDK1 specific activity, comparing a second threshold value with the CDK2 expression level, and comparing a third threshold value with the CDK4 expression level; and
   predicting the chemotherapy is effective when the CDK1 specific activity is higher than the threshold value, or when the CDK1 specific activity is not higher than the threshold value, the CDK2 expression level is higher than the second threshold value, and the CDK4 expression level is higher than the third threshold value.

2. The method according to claim 1, further comprising a second comparing step of comparing a second threshold value with an expression level of a cyclin dependent kinase inhibitor (CDK inhibitor),
   wherein the predicting step is carried out by predicting the effectiveness based on the comparison result and a second comparison result of the second comparing step.

3. The method according to claim 2, wherein the CDK is CDK2.

4. The method according to claim 2, wherein the parameter is the ratio of activity to expression level.

5. The method according to claim 2, wherein the CDK inhibitor is p21.

6. The method according to claim 1, further comprising:
   a second comparing step of comparing a second threshold value with an expression level of a cyclin dependent kinase inhibitor (CDK inhibitor); and
   a second predicting step of predicting the effectiveness based on the comparison result and a second comparison result of the second comparing step,
   wherein the second comparing step and the predicting step are executed in case the effectiveness is indeterminable in the predicting step.

7. The method according to claim 1, wherein the anticancer agent is selected from the group consisting of CMF and a taxane-based anticancer agent.

8. The method according to claim 1, wherein the tumor cell is collected from the human patient before the chemotherapy.

9. The method according to claim 1, wherein the tumor cell is a cell of adenocarcinoma of a breast.

* * * * *